United States Patent [19]

Scoggin

[11] 4,024,191

[45] May 17, 1977

[54] FRACTIONAL DISTILLATION PROCESS

[75] Inventor: Jack S. Scoggin, Bartlesville, Okla.

[73] Assignee: Phillips Petroleum Company, Bartlesville, Okla.

[22] Filed: Apr. 1, 1976

[21] Appl. No.: 672,811

[52] U.S. Cl. .............................. 260/609 D; 203/68; 203/70; 260/609 C
[51] Int. Cl.² ..................................... C07C 149/28
[58] Field of Search ........... 203/68, 70; 260/609 C, 260/609 D

[56] References Cited

UNITED STATES PATENTS

| | | | |
|---|---|---|---|
| 2,490,257 | 12/1949 | Crowley et al. | 260/609 D |
| 2,581,344 | 1/1952 | Anderson | 203/68 |
| 3,490,998 | 1/1970 | Jones | 260/609 C |
| 3,799,989 | 3/1974 | Sherk et al. | 260/609 D |

FOREIGN PATENTS OR APPLICATIONS 1,518,240  8/1965  Germany .............................. 203/68

Primary Examiner—Delbert R. Phillips

[57] ABSTRACT

In the fractional distillation of multicomponent mixtures where freezing of a component is encountered in the overhead condensing section and/or product decomposition is encountered at reboiling temperatures, these problems are obviated by carrying out the distillation in the presence of an added inert liquid which is somewhat more volatile than the component having a tendency to freeze. In one embodiment, the reaction effluent obtained in the production of thiophenol is subjected to fractional distillation wherein the distillation is carried out in the presence of a light hydrocarbon having a lower boiling point than an aromatic such as benzene so as to prevent freezing of benzene in the overhead condenser and at the same time lower the reboiler temperature to minimize thiophenol product decomposition.

12 Claims, 1 Drawing Figure

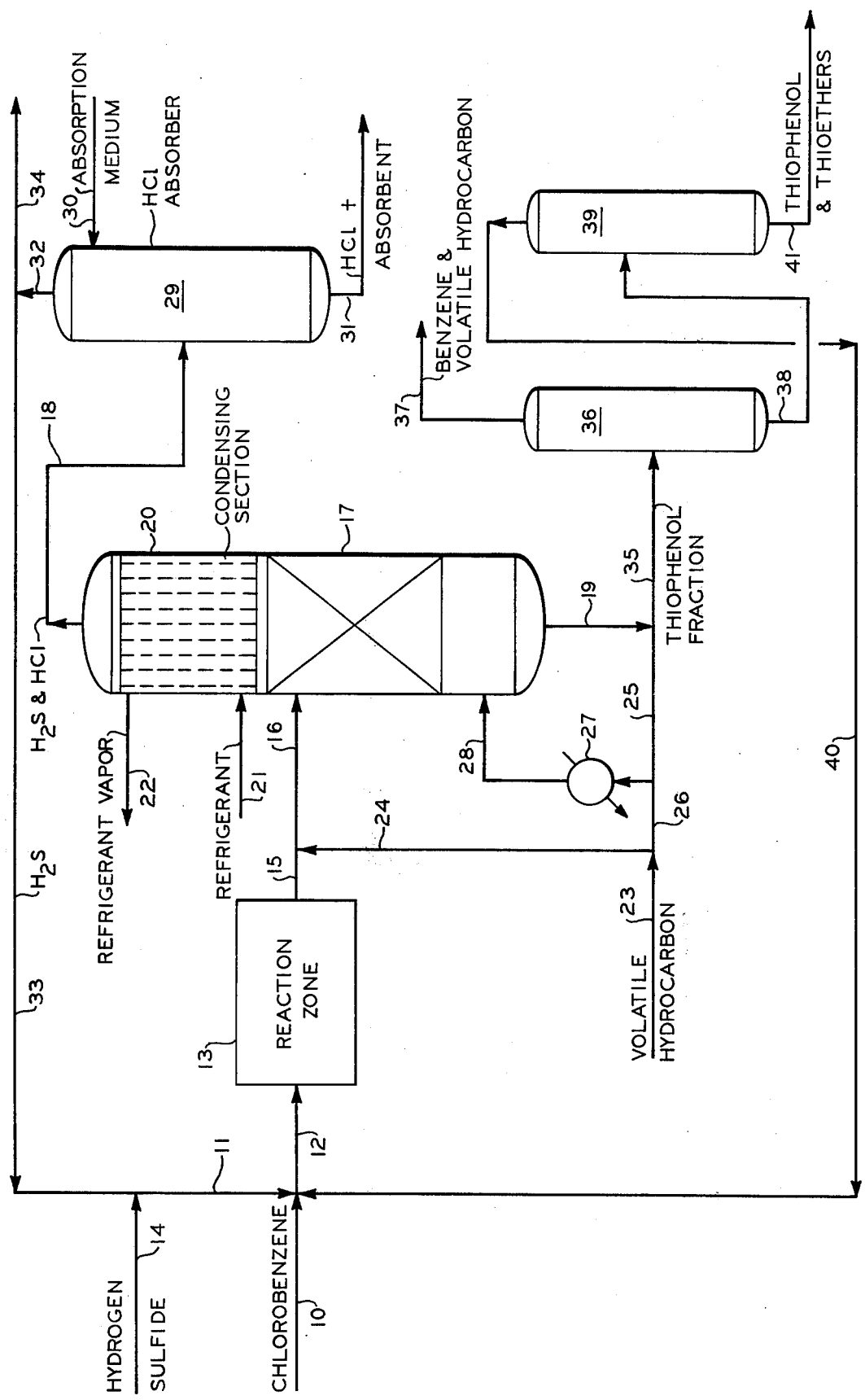

FRACTIONAL DISTILLATION PROCESS

This invention relates to fractional distillation. In accordance with another aspect, this invention relates to an improved fractional distillation process for the separation of multicomponent mixtures in which one of the components causes freezing in the overhead condensing section by addition of an external inert material or agent more volatile than the component causing the freezing. In accordance with a further aspect, this invention relates to the separation of acid gases in the effluent from an aromatic thiol process wherein the effluent is subjected to fractional distillation in the presence of an extraneous component for the dual purpose of prevention of overhead condenser freeze-up and decomposition of bottoms product. In accordance with a further aspect, this invention relates to introduction of a relatively volatile hydrocarbon component to a fractionator system, separating the reaction effluent contained in the production of thiophenol, which added component has a lower boiling point than benzene, one of the components being separated, for the dual purpose of eliminating freezing of benzene in the overhead condenser and lowering reboiler temperature to minimize thiophenol product decomposition and equipment corrosion.

The separation of multicomponent mixtures by fractional distillation is well known. One problem encountered in the fractional distillation of some multicomponent mixtures, especially where low temperatures are required to condense the overhead, is the freezing of one of the components in the mixture in the overhead condenser. As an example of one recovery process encountering freezing difficulties and other problems in the recovery of thiophenol from the product of the reaction of monochlorobenzene with hydrogen sulfide, as disclosed in U.S. Pat. No. 3,799,989, several problems are encountered:

1. It is desirable to maintain product processing temperatures as low as possible, preferably below about 425° F (218° C) to minimize equipment corrosion and product decomposition;
2. The acid gases should be separated essentially benzene-free to avoid loss of that valuable by-product; and
3. Freezing of benzene in condensers should be avoided.

In accordance with the invention, it has been found that the above problems can be avoided or solved by the addition of an extraneous component to fractional distillation operations for the dual purpose of prevention of overhead condenser freeze-up and decomposition of bottoms product.

Accordingly, an object of this invention is to provide an improved fractional distillation process.

Another object of this invention is to provide a fractional distillation process whereby overhead condenser freeze-up is avoided.

Another object of this invention is to provide an improved fractional distillation process in which decomposition of bottoms product is avoided.

A further object of this invention is to provide an external agent for fractional distillation to prevent freezing of distillate in an overhead condenser.

Other objects, aspects, and the several advantages of the invention will be apparent to those skilled in the art upon a study of the specification, the drawing, and the appended claims.

Broadly, according to the invention, an improved fractional distillation process is provided by carrying out the distillation in the presence of an added extraneous component to prevent freezing of distillate in the overhead condensing section and/or bottoms product decomposition and attendant equipment corrosion encountered at reboiling temperature. The added extraneous component should have a boiling point and freezing point lower than the distillate component going overhead that has a tendency to freeze in the condensing section.

More specifically, in accordance with one embodiment of the invention, in the recovery of thiophenol from the reaction effluent comprising acid gases, thiophenol, and converted reactants, thioethers, etc., the reaction effluent is passed to a fractional distillation zone and subjected to distillation conditions in the presence of an added extraneous component that is more volatile than an aromatic such as benzene to prevent freezing of aromatic distillate in the overhead condenser and at the same time lowering reboiler temperature to minimize thiophenol product decomposition and equipment corrosion. The extraneous component added to the fractional distillation is an inert liquid diluent such as a light hydrocarbon.

In accordance with one preferred embodiment, for the separation of a reaction effluent comprising thiophenol, acid gases, benzene, aromatic thioethers, and other materials are passed to a fractional distillation zone and distilled in the presence of an added light hydrocarbon lower boiling than benzene so as to prevent freezing of benzene in the overhead condenser and at the same time preventing decomposition of thiophenol product in the bottom by lowering the reboiler temperature.

As indicated above, it has been found that all three of the problems encountered in the recovery of thiophenol can be avoided or solved by the addition of an inert liquid which is somewhat more volatile than benzene to the reactor effluent before it passes to the separation zone, preferably one or more fractionators. Addition of the inert liquid serves to quench and partially condense the reactor effluent before passing to fractionation, to dilute and displace benzene in the condensing and rectifying zones and to dilute and thus lower the boiling point of the product and heavier mixture in the stripping and reboiler zones of the fractionator.

The preferred inert liquid diluent is a light hydrocarbon such as n-pentane. Other light hydrocarbons useful in the recovery of thiophenol include all the saturated paraffins in the $C_4$-$C_6$ range and naphthenes such as cyclopentane and methylcyclopentane which have lower boiling points than benzene and also very low freezing points.

The amount of light hydrocarbon added to the feed or to the distillation zone will be sufficient to prevent benzene from being taken overhead and at the same time lower the boiling point of the bottoms product being removed from the distillation zone. Generally, the amount of added light hydrocarbon will be in the range of 0.2–60 mols light hydrocarbon per mol of benzene. The lower end of this range, say 0.2–10 mols light hydrocarbon per mol of benzene, is adequate to prevent benzene freezing in the condenser; the higher end of this range is useful where it is desirable to obtain further lowering of the reboiler temperature.

Referring now to the drawing, there are shown diagrammatically the steps of the inventive process in terms of thiophenol production. Chlorobenzene and hydrogen sulfide are introduced by lines 10 and 11, respectively, to conduit 12 for introduction into reaction zone 13. Fresh hydrogen sulfide is introduced into the system by way of line 14. The conditions and other reaction parameters for the production of thiophenol from chlorobenzene and $H_2S$ are disclosed in U.S. Pat. No. 3,799,989 which patent is incorporated herein by reference.

A reaction effluent comprising thiophenol, HCl, $H_2S$, unconverted chlorobenzene, benzene, as well as diphenyl disulfide and other sulfur-containing materials is removed from reaction zone 13 by way of line 15. The reaction effluent is passed by way of line 16 and introduced into fractional distillation zone 17. The reaction effluent introduced into fractional distillation zone 17 is subjected to contacting conditions such that $H_2S$ and HCl are taken overhead, and the remainder of the feed is removed as bottoms by way of line 19. In the upper portion of distillation zone 17, there is located a refrigerated condensing section 20. A refrigerant introduced by line 21 is circulated through condensing section 20, and refrigerant vapor is withdrawn at line 22. Generally, some benzene tends to go overhead through condensing section 20 and causes freeze-up in the condensing section.

In accordance with the invention, in order to eliminate or substantially prevent carryover of benzene into the condensing section and causing freeze-up, a volatile hydrocarbon such as normal pentane is introduced by line 23 and line 24 for introduction into the reaction effluent in lines 15 and 16. Together with volatile hydrocarbon introduced by way of line 23, a portion of the bottoms product removed by line 19 is passed by way of lines 25 and 26 and combined with the volatile hydrocarbon for introduction into the thiophenol reaction effluent. The mixed stream introduced by way of line 24 serves in part to quench the reaction effluent prior to introduction into distillation zone 17. A portion of the bottoms thiophenol fraction in line 25 is passed to reboiler 27 and then reintroduced into the lower portion of 17 by way of line 28.

The amount of volatile hydrocarbon such as normal pentane introduced into the thiophenol reaction effluent is sufficient to prevent benzene from being carried overhead in zone 17, thereby avoiding freeze-up in condensing section 20. At the same time, the amount of volatile hydrocarbon added is sufficient to reduce the reboiler temperature sufficiently to prevent thiophenol decomposition.

The overhead of $H_2S$ and HCl and some n-pentane removed by line 18 is passed to HCl absorber 29 wherein the stream is contacted with an absorption medium introduced by line 30 for absorption of HCl which is removed together with absorbent from the base of zone 29 by line 31. Overhead comprising $H_2S$ is removed from zone 29 by way of line 32, and, if desired, a portion of it can be recycled to zone 13 by way of line 33. The remainder of the $H_2S$ can be sent to further processing by way of line 34, if desired.

A portion of the thiophenol fraction removed from the lower portion of zone 17 is passed by line 35 to further fractionation or other separation zone 36 wherein benzene and previously added volatile hydrocarbon are taken overhead by line 37 and chlorobenzene, thiophenol, and thioether are removed as bottoms by way of line 38. The latter stream can be further separated in fractionation or other separation zone 39 to recover unconverted chlorobenzene overhead which may be removed and recycled via lines 40 and 12 to reaction zone 13. Thiophenol and thioether bottoms 41 may be further separated, as desired.

In the preceding description of the drawings, the four columns 17, 29, 36, and 39, as well as other separation zones not described, are all operated under conditions of temperature and pressure and suitable equipment to effect the separations described. In zone 17, low temperatures are required to condense the overhead so as to condense substantially only $H_2S$, HCl, and added volatile hydrocarbon, thus avoiding loss of benzene and minimizing loss of the volatile hydrocarbon. Thus, the condensing section is operated at a temperature such that vapors are removed overhead by way of line 18 at about 0° C. The bottom portion of column 17 is operated at temperatures of about 200° C. Generally, the upper portion of column 17 could be operated at a temperature in the range of −10° C to +20° C and the bottom at a temperature of 177° C to 230° C.

The diagrammatic process scheme of the drawing is, of course, greatly simplified for convenience. Not shown are important items such as heat exchangers, hold tanks, valves, pumps, control apparatus, etc. These are within the skills of those employed in this art.

Although the drawing and the subsequent example have specifically illustrated the invention process as applied to the production of thiophenol, those skilled in the art will appreciate that the invention is also applicable to other homologous and analogous feeds and products.

EXAMPLE

A reaction effluent stream obtained from the reaction of chlorobenzene and hydrogen sulfide is passed to a fractional distillation zone 17 such as described in connection with the drawing. The distillation apparatus is provided with 22 theoretical stages and an internal condensing section in the upper portion of the column to which refrigerant is circulated to maintain the upper portion of the column at approximately 0° C. A portion of the thiophenol bottoms product is returned to the column by way of a reboiler and another portion is returned to the column after combining with the reaction effluent feed to the column.

In accordance with the invention, normal pentane is introduced into the bottoms product recycled to the reaction effluent feed being passed to zone 17.

Based upon mols per stream day, the feed composition, the overhead and bottoms products are set forth below in the following table.

| Stream | Reaction Effluent 15 | n-Pentane 23 | Overhead 18 | Bottoms 35 |
|---|---|---|---|---|
| $H_2S$ | 412.4 | | 412.4 | 19 ppm |
| HCl | 148.5 | | 148.5 | 1 ppm |
| $CO_2$ | 48.0 | | 48.0 | |
| n-Pentane | | 133.0 | 6.0 | 127 |
| Benzene | 5.8 | | | 5.8 |
| Chlorobenzene | 80.0 | | | 80.0 |
| Thiophenol | 125.7 | | | 125.7 |
| Diphenyl sulfide | 54.1 | | | 54.1 |
| Diphenyl disulfide | 7.4 | | | 7.4 |
| | 881.9 | 133.0 | 614.9 | 400.0 |

The above tabulation illustrates that the addition of n-pentane to the thiophenol reaction effluent prevents carryover of benzene into the condensing section and thereby avoids freeze-up in the condensing section as all of the benzene is withdrawn with bottoms product.

I claim:

1. A method for separating $H_2S$ and HCl overhead from admixture with benzene and thiophenol by fractional distillation without freezing of benzene in the overhead condensers which comprises adding a sufficient amount of a light hydrocarbon having a boiling point lower than benzene to said admixture being fed to said fractional distillation to prevent benzene from being taken overhead and to lower the bottoms temperature sufficiently to minimize thiophenol product decomposition.

2. A method according to claim 1 wherein the light hydrocarbon is a paraffin or naphthene having from 4 to 6 carbon atoms.

3. A method according to claim 1 wherein the amount of light hydrocarbon added with respect to benzene is in the range of 0.2 to 60 on a molal basis.

4. A method according to claim 1 wherein the light hydrocarbon is n-pentane and the amount of n-pentane added with respect to benzene is in the range of 0.2 to 60 on a molal basis.

5. A method for separating a multicomponent mixture by fractional distillation in which freezing of at least one component is encountered in the condensing section, the improvement for preventing overhead condenser freeze-up which comprises adding to said multicomponent mixture an extraneous inert material having a higher volatility and a lower freezing point than said one component, the amount of said extraneous material added to said distillation being sufficient to prevent said one component from being taken overhead from said distillation and thereby preventing overhead condenser freeze-up.

6. A method according to claim 5 wherein the light hydrocarbon is a paraffin or naphthene having from 4 to 6, inclusive, carbon atoms.

7. A method according to claim 5 wherein the amount of said extraneous component with respect to said one component during said distillation is in the range of 0.2 to 60 on a molal basis.

8. A method for separating the effluent for producing aromatic thiols by reacting an aryl halide and $H_2S$ which comprises:

a. reacting at least one aryl halide with $H_2S$ under reaction conditions including an elevated temperature and a time sufficient to form a reaction effluent comprising aromatic thiol, hydrogen halide, $H_2S$, unreacted aryl halide, aromatic, and aromatic thioethers, b. passing said reaction effluent as feed to a fractional distillation zone, c. introducing into said fractional distillation zone a paraffinic or naphthenic hydrocarbon lower boiling than said aromatic, the amount of added hydrocarbon being sufficient to prevent said aromatic from being taken overhead from said distillation zone, and d. subjecting said feed and added hydrocarbon to fractional distillation conditions to take as overhead hydrogen halide, $H_2S$, and some of said added hydrocarbon, but substantially free of said aromatic, and as bottoms aromatic thiol, added hydrocarbon, and aromatic thioethers.

9. A method according to claim 8 wherein said light hydrocarbon added to said distillation is a paraffin or naphthene having from 4 to 6, inclusive, carbon atoms, and the amount of hydrocarbon added to said distillation with respect to said aromatic is in the range of 0.2 to 60 on a molal basis.

10. A method according to claim 8 wherein said aromatic thiol is thiophenol, said hydrogen halide is HCl, said aromatic hydrocarbon is benzene, and said added extraneous hydrocarbon is n-pentane, and the amount of n-pentane added to said distillation with respect to benzene is in the range of 0.2 to 60 on a molal basis.

11. A method according to claim 10 wherein the n-pentane added to said distillation is introduced into the reboiler section of said distillation so as to lower the bottoms temperature sufficiently to minimize thiophenol product decomposition.

12. A method according to claim 8 wherein the hydrocarbon added to said fractional distillation column in (c) is combined with a portion of the bottoms removed from said fractional distillation column and the mixed stream thus formed is mixed with feed passed to said distillation so as to serve in part to quench the reaction effluent prior to introduction into the distillation zone and to lower the bottoms temperature sufficiently to minimize thiophenol product decomposition.

* * * * *